US007829543B2

(12) United States Patent
Nelson et al.

(10) Patent No.: US 7,829,543 B2
(45) Date of Patent: Nov. 9, 2010

(54) SUBSTITUTED POLYAMINES AS INHIBITORS OF BACTERIAL EFFLUX PUMPS

(75) Inventors: Mark L. Nelson, Norfolk, MA (US); Michael N. Alekshun, Wakefield, MA (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 688 days.

(21) Appl. No.: 10/754,041

(22) Filed: Jan. 7, 2004

(65) Prior Publication Data

US 2004/0204378 A1    Oct. 14, 2004

Related U.S. Application Data

(60) Provisional application No. 60/438,725, filed on Jan. 7, 2003, provisional application No. 60/438,653, filed on Jan. 8, 2003, provisional application No. 60/438,754, filed on Jan. 8, 2003.

(51) Int. Cl.
*A61K 31/7036* (2006.01)
*A61K 31/70* (2006.01)
*A61K 31/715* (2006.01)

(52) U.S. Cl. .................... 514/39; 514/36; 514/673; 514/54

(58) Field of Classification Search .............. 514/39, 514/36, 674, 54, 673; 415/673
See application file for complete search history.

(56) References Cited

U.S. PATENT DOCUMENTS

| 2,916,485 | A | | 12/1959 | Frohardt et al. |
| 5,900,406 | A | | 5/1999 | Von Ahsen et al. |
| 6,068,972 | A | * | 5/2000 | Levy .................... 435/4 |
| 6,136,771 | A | * | 10/2000 | Taylor et al. ............ 510/388 |
| 6,204,297 | B1 | | 3/2001 | Tracy et al. |
| 6,326,391 | B1 | | 12/2001 | Markham et al. |
| 6,346,391 | B1 | * | 2/2002 | Oethinger et al. ......... 435/32 |
| 6,436,980 | B1 | | 8/2002 | Leger et al. |

FOREIGN PATENT DOCUMENTS

| DE | 2515629 A1 | 4/1975 |
| EP | 021150 A1 | 3/1980 |
| EP | 349224 A2 | 1/1990 |
| EP | 349224 A3 | 1/1990 |
| WO | WO 96/33285 A1 | 10/1996 |
| WO | WO 97/31917 A1 * | 9/1997 |
| WO | WO 99/17760 A2 | 4/1999 |
| WO | WO 99/37667 A1 | 7/1999 |
| WO | WO 00/01714 A1 | 1/2000 |
| WO | WO 02/09758 A1 | 2/2002 |
| WO | WO 2004/024140 A1 | 3/2004 |
| WO | WO 2004/062674 A2 | 7/2004 |

OTHER PUBLICATIONS

Fujii et al., The Journal of Antibiotics, (Tokyo), May 1968, vol. 21. No. 5, pp. 340-349.*
Forsee et al.,Journal of the American Chemical Society, (1935), vol. 57, pp. 1788-1799 (Abstract Sent).*
Stetter et al., Chemische Berichte (1973), vol. 106, No. 8, pp. 2523-2529. (Abstract Sent).*
Schulze et al., DD 248500 A1, Aug. 12, 1987.(Abstract Sent).*
Arct et al. (Przemysl Chemiczny (1962), 41, 582-6 (Abstract Sent)).*
Eckstein et al. (Bulletin de l'Academie Polonaise des Sciences, Serie des Sciences Chimiques (1962), 10, 487-92) (Abstract Sent).*
Reichert et al. (Arch. Pharm.(1944), 282, 109-12)(Abstract Sent).*
Stetter et al., Chemische Berichte (1973), vol. 106, No. 8, pp. 2523-2529. (Abstract Sent).*
Bollinger et al. (Conference on Coordination Chemistry (1995), 15th (Current Trends in Coordination Chemistry), 361-6) (Abstract sent).*
Arcamone, F.M., et al.. "New semisynthetic aminosidine derivatives." *G Ital Chemioter*. Jan.-Dec. 1977; 24(1-2):77-81.
Aires, J.R., et al., "Involvement of an active efflux system in the natural resistance of *Pseudomonas aeruginosa* to aminoglycosides." *Antimicrob Agents Chemother*. Nov. 1999; 43(11):2624-8.
Cassinelli, G., et al., "Semisynthetic aminoglycoside antibiotics. I. New reactions of paromomycin and synthesis of its 2'-N-ethylderivative." *J Antibiot* (Tokyo). Apr. 1978, 31(4):379-81.
Chen, H.Y., et al., "Identification and analysis of the sap genes from *Vibrio fischeri* belonging to the ATP-binding cassette gene family required for peptide transport and resistance to antimicrobial peptides." *Biochem Biophys Res Commun*. Mar. 24, 2000; 269(3):743-8.
Elkins, C.A., et al., "Substrate specificity of the RND-type multidrug efflux pumps AcrB and AcrD of *Escherichia coli* is determined predominantly by two large periplasmic loops." *J Bacteriol*. Dec. 2002; 184(23):6490-8.
Fath, M.J., et al., "ABC transporters: bacterial exporters." *Microbiol Rev*. Dec. 1993; 57(4):995-1017.
Fujii, A., et al. "Synthesis of tetra-N-phenylalkylkanamycins and their antimicrobial activities." *J Antibiot* (Tokyo). May 1968;21(5):340-9.

(Continued)

*Primary Examiner*—Shaojia Anna Jiang
*Assistant Examiner*—Michael C Henry
(74) *Attorney, Agent, or Firm*—McCarter & English, LLP; Elizabeth A. Hanley; Meaghan L. Richmond

(57) ABSTRACT

Disclosed are methods of treating bacterial infections including those caused by multidrug resistant bacteria using polyamine efflux pump inhibiting compounds, including for example N-benzylated polyazaalkanes, N-benzylated polyaminoalkanes, or mixed N-benzylated poly(aza/amino) alkanes, optionally in combination with other drugs such as antibiotics, as well as pharmaceutical compositions thereof.

20 Claims, No Drawings

OTHER PUBLICATIONS

Jones, R.N., et al., "Comparative spectrum and activity of NVP-PDF386 (VRC4887), a new peptide deformylase inhibitor." *J Antimicrob Chemother*. Jan. 2003; 51(1):157-61.

Levy, S.B., "Active efflux mechanisms for antimicrobial resistance." *Antimicrob Agents Chemother*. Apr. 1992; 36(4):695-703.

Ma, D., et al., "Molecular cloning and characterization of acrA and acrE genes of *Escherichia coli*." *J Bacteriol*. Oct. 1993; 175(19):6299-313.

Nikaido, H., "Multidrug efflux pumps of gram-negative bacteria." *J Bacteriol*. Oct. 1996; 178(20):5853-9.

Nikaido, H., et al.. "Multidrug efflux pump AcrAB of *Salmonella typhimurium* excretes only those beta-lactam antibiotics containing lipophilic side chains." *J Bacteriol*. Sep. 1998; 180(17):4686-92.

Ouellette, M., et al., "Microbial multidrug-resistance ABC transporters." *Trends Microbiol*. Oct. 1994; 2(10):407-11.

Rengaraju, S., et al., "3-N-methylparomomycin I produced by a Streptomyces." *J Antibiot* (Tokyo). Nov. 1986; 39(11):1598-601.

Rosenberg, E.Y., et al., "AcrD of *Escherichia coli* is an aminoglycoside efflux pump." *J Bacteriol*. Mar. 2000; 182(6):1754-6.

Sanchez, L., et al., "The acrAB homolog of *Haemophilus influenzae* codes for a functional multidrug efflux pump." *J Bacteriol*. Nov. 1997; 179(21):6855-7.

Spratt, B.G., "Resistance to antibiotics mediated by target alterations." *Science*. Apr. 15, 1994; 264(5157):388-93.

Stermitz, F.R., et al., "Synergy in a medicinal plant: antimicrobial action of berberine potentiated by 5'-methoxyhydnocarpin, a multidrug pump inhibitor." *Proc Natl Acad Sci U S A*. Feb. 15, 2000; 97(4):1433-7.

Sutcliffe, *Curr. Opin. Anti-infect. Invest. Drugs*. 1999; 1:403-12.

Taniyama, H., et al., "Antibiotics aminosidin. II. Some amino derivatives of aminosidin and their biological activity." *Chem Pharm Bull* (Tokyo). Mar. 1973; 21(3):609-15.

Tomitori, H., et al., "Identification of a gene for a polyamine transport protein in yeast." *J Biol Chem*. Feb. 5, 1999; 274(6):3265-7.

Westbrock-Wadman, S., et al., "Characterization of a *Pseudomonas aeruginosa* efflux pump contributing to aminoglycoside impermeability." *Antimicrob Agents Chemother*. Dec. 1999; 43(12):2975-83.

Woolridge, D.P., et al., "Characterization of a novel spermidine/spermine acetyltransferase, BltD, from *Bacillus subtilis.*" *Biochem J*. Jun. 15, 1999; 340 (Pt.3):753-8.

Woolridge, D.P., et al., "Efflux of the natural polyamine spermidine facilitated by the *Bacillus subtilis* multidrug transporter Blt." *J Biol Chem*. Apr. 4, 1997; 272(14):8864-6.

\* cited by examiner

SUBSTITUTED POLYAMINES AS INHIBITORS OF BACTERIAL EFFLUX PUMPS

RELATED APPLICATIONS

This application claims priority to U.S. Provisional Patent Application No. 60/438,754, "Substituted Polyamines as Inhibitors of Bacterial Efflux Pumps" filed on Jan. 8, 2003, U.S. Provisional Patent Application No. 60/438,653, "Substituted Polyamines as Inhibitors of Bacterial Efflux Pumps" filed on Jan. 8, 2003, and to U.S. Provisional Patent Application No 60/438,725, "Substituted Polyamines as Inhibitors of Bacterial Efflux Pumps" filed on Jan. 7, 2003. The entire contents of each of these patent applications are hereby incorporated herein by reference.

BACKGROUND

Microbes have developed several different mechanisms of resistance to antibiotics and chemotherapeutic agents. These mechanisms of resistance can be specific, e.g., for a molecule or a family of molecules (e.g., antibiotics), or can be non-specific and be involved in resistance to unrelated antibiotics or other molecules. Several mechanisms of resistance can exist in a single bacterial strain, and those mechanisms may act independently or they may act synergistically to overcome the action of an antibiotic or a combination of antibiotics. Specific mechanisms include degradation of the drug, inactivation of the drug by enzymatic modification, and alteration of the drug target (Spratt (1994) *Science* 264, 388). There are, however, more general mechanisms of drug resistance, in which access of the antibiotic to the target is prevented or reduced by decreasing the transport of the antibiotic into the cell or by increasing the efflux of the drug from the cell to the outside medium. Both mechanisms can lower the concentration of drug at the target site and allow bacterial survival in the presence of one or more agents which would otherwise inhibit the growth of or kill the bacterial cells.

Efflux pumps are involved in the efflux of drugs from microbial cells. Once in the cytoplasm or periplasm, a drug can be transported back to the outer medium by such membrane-bound protein pumps. Different pumps a specific for a drug or group of drugs, such as the NorA system that transports quinolones, or Tet A that transports tetracyclines, or they can efflux a large variety of molecules, such as certain efflux pumps of *Pseudomonas aeruginosa*. In general, efflux pumps have a cytoplasmic component and energy is required to transport molecules out of the cell.

Efflux membrane proteins are distributed among microbes, e.g., Gram-positive and Gram-negative bacteria and are involved in transmembrane export of different substances such as heavy metals, organic solvents, dyes, disinfectants and antibiotics (Lawrence, et al. (1998.) *Exp. Opin. Invest. Drugs* 7, 199-217; Levy (1992) *Antimicrob. Agents Chemother.* 36, 695-703; Nikaido (1996) *J. Bacteriol.* 178, 5853; and Sutcliffe (1999) *Curr. Opin. Anti-infect. Invest. Drugs* 1, 403). Efflux proteins have been broadly classified into five groups: the ATP-binding cassette (ABC) transporters (Fath, et al. (1993) *Microbiol. Rev.* 57, 995; Ouellette, et al. (1994) *Trends in Microbiology* 2, 407); RND (Resistance Nodulation and Cell Division, e.g., *E. coli* AcrB and *P. aeruginosa* MexB), SMR (Staphylococcal or Small Multi-drug Resistance, e.g., *S. aureus* Smr), MF or MFS (Major Facilitator Superfamily, e.g., all of the Tet efflux proteins, NorA from *S. aureus*, and Bmr from *B. subtilis*), and MATE (Multidrug and Toxin Extrusion, e.g., NorM from *Vibrio parahaemolyticus*).

The exact physiological role of efflux pumps has not yet been clearly defined. Microbial pumps appear to remove intracellular nitrogenous toxins, including polyamines, e.g., spermidine and spermine (Woolridge, et al. (1997) 272, 8864; Woolridge, et al. (1999) *Biochem. J.* 340, 753), peptides and peptidomimetics (Chen, et al. (2000) *Biochem. Biophys. Res. Commun.* 269, 743), and antibiotics, e.g., aminoglycosides (Aires, et al. (1999) 43, 2624; Westbrock-Wadman, et al. (1999) 43, 2975; Elkins, et al. (2002) *J. Bacteriol.* 184(23), 6490; Rosenberg, et al. (2000) *J. Bacteriol.* 182(6), 1754), allowing cellular survival. They are involved in drug resistance but they also may be involved in the normal physiology of the bacterial cell. For example, the efflux pump coded in the mexA operon of *P. aeruginosa* has been shown to be regulated by the iron content of the medium, and it is co-regulated with the synthesis of the receptors of siderophores. Siderophores are molecules that are needed for bacterial growth under iron starvation conditions, such as during infection of an animal. They are synthesized in the cytoplasm and exported when the bacterial cell needs iron. Siderophores scavenge iron within the infected animal and return the iron to the microbe to be used for essential microbial processes. Since there is essentially no free iron in the bodies of animals, including the human body, the production of siderophores by infecting bacteria is an important virulence factor for the progress of the infection.

Drug efflux proteins in microbes can mediate resistance causing therapeutic failures. The identification of agents that inhibit the activity of efflux pumps would be of great benefit.

SUMMARY OF THE INVENTION

The instant invention advances the prior art by providing compositions which are useful in inhibiting microbial efflux pumps. Owing to their ability to inhibit efflux, these compounds are useful in inhibition of microbial growth (e.g., in a subject or on surfaces) or in treating infection (e.g., in an animal or plant subject) as well as in reducing microbial virulence. Accordingly, disclosed are methods of treating bacterial infections, including infections with multidrug resistant bacteria, polyamine efflux pump inhibiting compounds, including for example N-benzylated polyazaalkanes, N-benzylated polyaminoalkanes, or mixed N-benzylated poly(aza/amino)alkanes as well as pharmaceutical compositions thereof. In one embodiment, the efflux pump inhibitors of the invention can be used in combination with one or more other drugs, such as antibiotics or biocides.

In one aspect, the invention relates to an inhibitor of an efflux pump for treating an infection caused by a microbe in a subject, wherein the inhibitor is a polyamine in which at least two nitrogens are substituted with a lipophilic group. In particular, the lipophilic group may be a substituted or unsubstituted N-benzyl group.

As used herein, a "polyamine" is, for example, a polyazaalkane, polyaminoalkane, or mixed poly(aza/amino)alkane, any carbon atom of which may be hydroxyl, amino, or oxo substituted.

The invention also relates to a method for treating a microbial infection in an animal, comprising administering an efflux pump inhibitor in an amount sufficient to reduce efflux pump activity using compounds of the invention.

Similarly, the invention embraces a method of treating an infection caused by a microbe in a subject comprising administering an inhibitor of an efflux pump that is a compound of the invention.

Additionally, the present invention includes a method of enhancing the antimicrobial activity of an antimicrobial agent against a microbe, comprising contacting said microbe with said antimicrobial agent and an efflux pump inhibitor compound of the invention.

In another embodiment, the invention relates to a method of enhancing the antimicrobial activity of a drug comprising contacting a microbe that is resistant to one or more drugs with a drug to which the microbe is resistant and an inhibitor compound of the invention that is an inhibitor of an efflux pump to thereby enhance the antimicrobial activity of a drug.

Accordingly, the invention relates to a pharmaceutical composition for use in the methods of the invention. In one such embodiment, the invention relates to a pharmaceutical composition effective for treatment of an infection of an animal by a microbe, comprising an efflux pump inhibitor compound of the invention and a pharmaceutically acceptable carrier.

In another aspect, the invention relates to a composition comprising a non-antibiotic bactericidal or bacteriostatic first agent and a second agent that inhibits the expression or activity of an efflux pump, wherein said inhibitor is a compound of the invention.

Furthermore, the invention pertains to a pharmaceutical composition comprising an antibiotic and an inhibitor of an efflux pump selected from the group consisting of N-benzylated polyamines, including N-benzylated polyazaalkanes, N-benzylated polyaminoalkanes, or mixed N-benzylated poly(aza/amino)alkanes, any carbon atom of which may be hydroxyl, amino, or oxo substituted.

Inhibitors of bacterial efflux pumps may generally be made by the chemical modification of polyamines, aminoglycosides, and other amine containing scaffolds. Suitable chemical modifications may increase the affinity of the nitrogenous substrate for bacterial antibiotic efflux proteins, thereby decreasing the translocation of these agents across the bacterial membrane. These efflux blocking compounds may be administered alone to inhibit the efflux of microbial waste products or environmental toxins or with a drug (e.g., an antibiotic or non-antibiotic agent to increase susceptibility to the drug.

DETAILED DESCRIPTION OF THE INVENTION

As noted above, disclosed are methods of inhibiting the efflux of compounds, methods of inhibiting microbial growth (e.g., in a subject or on surfaces), methods of treating infection (e.g., in an animal or plant subject), as well as methods of reducing microbial virulence in microbes, including multi-drug resistant bacteria, using polyamine compounds, including for example N-benzylated polyazaalkanes, N-benzylated polyaminoalkanes, or mixed N-benzylated poly(aza/amino)alkanes, optionally in combination with other drugs such as antibiotics, as well as pharmaceutical compositions thereof.

As used herein, a "polyamine" is, for example, a polyazaalkane, polyaminoalkane, or mixed poly(aza/amino)alkane, any carbon atom of which may be hydroxyl, amino, or oxo substituted. Preferably, such polyamines do not have N—N, N—O, or O—O bonds. Furthermore, polyamines preferably have at least two nitrogen atoms that may be bound to a lipophilic group.

As used herein the term "infection" includes the presence of a microbe in or on a subject which, if its growth were inhibited, would result in a benefit to the subject. As such, the term "infection" in addition to referring to the presence of pathogens also includes the presence of normal flora which is not desirable, e.g., on the skin of a burn patient or in the gastrointestinal tract of an immunocompromised patient.

As used herein, the term "treating" includes the administration of an efflux pump inhibitor of the invention to a subject, for prophylactic or therapeutic purposes. The term "administration" includes delivery to a subject, e.g., by any appropriate method which serves to deliver the drug either systemically or to the site of the infection. Administration of the drug can be, e.g., oral, intravenous, or topical.

The term "efflux pump" refers to a protein assembly which exports substrate molecules from the cytoplasm or periplasm of a cell, in an energy dependent fashion. Thus, an efflux pump will typically be located in the cytoplasmic membrane of the microbial cell (spanning the cytoplasmic membrane). Efflux pumps can be present in Gram-negative or Gram-positive bacteria. In preferred embodiments, microbes for use in the claimed methods are bacteria, either Gram-negative or Gram-positive bacteria. In one embodiment, any bacteria that are shown to become resistant to antibiotics, e.g., to display MDR are appropriate for use in the claimed methods. Families of microbial efflux pumps include: RND (Resistance Nodulation and Cell Division, e.g., *E. coli* AcrB and *P. aeruginosa* MexB), SMR (Staphylococcal or Small Multidrug Resistance, e.g., *S. aureus* Smr), MF (Major Facilitator, e.g., all of the Tet efflux proteins, NorA from *S. aureus*, and Bmr from *B. subtilis*), and MATE (Multidrug and Toxin Extrusion, e.g., NorM from *Vibrio parahaemolyticus*) (Nikaido (1998) *Curr. Opinion in Microbiology* 1, 516; Markham and Neyfakh (2001) *Curr. Opinion in Microbiology* 4, 509; Poole (2001) *Curr. Opinion in Microbiology* 4, 500).

The MF superfamily of efflux pumps is comprised of transport proteins involved in the symport, antiport, or uniport of various substrates. The family comprises two distinct families of efflux pumps with 12 or 14 transmembrane segments. A number of highly conserved regions or motifs have been identified in members of the MF family (Griffith, et al. (1992) *Curr. Opin. Cell Biol.* 4, 684; Marger, et al. (1993) *Trends Biochem. Sci.* 18, 13; Paulsen and Skurray (1993) *Gene* 124, 1; Paulsen, et al. (1996) *Microbiological Reviews* 60, 575). For example, motifs have been identified which are conserved throughout the MF (motifs A and B), only in both the 12 and 14-TMS family (motif C), or exclusive to either the 112 or 14-TMS family (motifs D to G) (Paulsen and Skurray (1993) *Gene* 124, 1; Paulsen, et al. (1996) *Microbiological Reviews* 60, 575).

The SMR family proteins are typically around 110 amino acid residues in length with 4 predicted TMS. Multiple-sequence alignment of SMR family proteins shows that there are a number of residues which are absolutely conserved, implicating them in an essential structure of function (Paulsen, et al. (1996) *Microbiological Reviews* 60, 575; Paulsen, et al. (1996) *Mol. Microbiol.* 19, 1167).

The MATE family of efflux pumps is described in the art (Putman, et al. (2000) *Microbiol Mol. Biol. Rev.* 64, 672).

The RND family have a proposed structure that consists of 12 TMS with two large loops between TMS 1 and 2 and TMS 7 and 8 (Paulsen, et al. (1996) *Microbiological Reviews* 60, 575; Saier, et al. (1994) *Mol. Microbiol.* 11, 841). Comparative sequence analysis indicates that the N- and C-terminal halves of RND proteins share sequence similarity (Paulsen, et al. (1996) *Microbiological Reviews* 60, 575; Paulsen, et al. (1996) *Mol. Microbiol.* 19, 1167). In gram-negative bacteria, the genes for RND family proteins are frequently found in association with genes encoding members of thee MFP family. MFP proteins interact cooperatively to enable drug transport across both inner and outer membranes of gram-negative bacterial cells. In some cases, MFP proteins and their respective transport proteins have been proposed to interact with members of a third protein family, namely the OMF family (Ma, et al. (1994) *Trends Microbiol.* 2, 489; Paulsen, et al. (1996) *Microbiological Reviews* 60, 575). In a preferred embodiment, an efflux pump of the invention is an RND efflux pump.

In one embodiment, the efflux pump of the invention is an efflux pump that has similar biological function or homology with the acrAB efflux pump of *E. coli*, i.e., is an acrAB-like efflux pump (efflux pumps related to and including the acrAB pump). The acrAB pump is a resistance, nodulation, and division (RND)-type pump. The acrA and acrB genes have been cloned and sequenced (Ma, et al. (1993) *J. Bacteriol.* 175, 6229). The sequences of acrAB in *E. coli* are deposited as GenBank accession number U00734. The acrAB genes have other homologs in *E. coli*, as well as homologs in other species of bacteria. For example, homologs of the acrAB efflux pump have been identified in *Haemophilus influenzae*, (Sanchez, et al. (1997) *J. Bacteriol.* 179, 6855) and in *Salmonella typhimurium* (Nikaido, et al. (1998) *J. Bacteriol.* 180, 4686). Exemplary homologues of acrAB include MtrCD, MexAB-OprM, MexCD-OprJ, MexEF-OprN, and YhiUV.

Isolation of novel efflux pumps from any of these families microbes can be carried out using techniques which are known in the art, e.g., nucleic acid hybridization and functional cloning. Such homologs can be readily identified by one of ordinary skill in the art based on shared homology and structure with previously known efflux pumps or based on similarities in the compounds which they export. For example, members of efflux pump families share common properties, e.g., certain structural and functional characteristics are shared among the family members. Accordingly, it will be understood by one of ordinary skill in the art that the structural relatedness inquiries described below (e.g., based on primary nucleic acid or amino acid sequence homology (or on the presence of certain signature domains) or on hybridization as an indicator of such nucleic acid homology), or based on three-dimensional correspondence of amino acids) can be used to identify members of the various efflux pump families.

Efflux pumps belonging to particular families are "structurally related" to one or more known family members, e.g., members of the RND efflux pump family are structurally related to each other. This relatedness can be shown by sequence or structural similarity between two polypeptide sequences or between two nucleotide sequences that specify such polypeptides. Sequence similarity can be shown, e.g., by optimally aligning sequences using an alignment program for purposes of comparison and comparing corresponding positions. To determine the degree of similarity between sequences, they will be aligned for optimal comparison purposes (e.g., gaps may be introduced in the sequence of one protein for nucleic acid molecule for optimal alignment with the other protein or nucleic acid molecules). The amino acid residues or bases and corresponding amino acid positions or bases are then compared. When a position in one sequence is occupied by the same amino acid residue or by the same base as the corresponding position in the other sequence, then the molecules are identical at that position. If amino acid residues are not identical, they may be similar. As used herein, an amino acid residue is "similar" to another amino acid residue if the two amino acid residues are members of the same family of residues having similar side chains. Families of amino acid residues having similar side chains have been defined in the art (see, for example, Altschul, et al. (1990) *J. Mol. Biol.* 215, 403) including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan). The degree (percentage) of similarity between sequences, therefore, is a function of the number of identical or similar positions shared by two sequences (i e., % homology=# of identical or similar positions/total # of positions× 100). Alignment strategies are well known in the art, see, for example, Altschul, et al., supra, for optimal sequence alignment.

The nucleic acid or amino acid sequences of a known member of an efflux pump family can be used as "query sequences" to perform a search against databases (e.g., either public or private) to, for example, identify other family members having related sequences. Such searches can be performed, e.g., using the NBLAST and XBLAST programs (version 2.0) of Altschul, et al. (1990) *J. Mol. Biol.* 215, 403. BLAST nucleotide searches can be performed with the NBLAST program, score=100, wordlength=12 to obtain nucleotide sequences homologous to efflux pump family nucleic acid molecules. BLAST protein searches can be performed with the XBLAST program, score=50, wordlength=3 to obtain amino acid sequences homologous to efflux pumps of the invention. To obtain gapped alignments for comparison purposes, Gapped BLAST can be utilized as described in Altschul, et al. (1997) *Nucleic Acids Res.* 25, 3389. When utilizing BLAST and Gapped BLAST programs, the default parameters of the respective programs (e.g., XBLAST and NBLAST) can be used.

Efflux pump family members can also be identified as being similar based on their ability to specifically hybridize to nucleic acid sequences specifying a known member of a efflux pump family. Such stringent conditions are known to those skilled in the art and can be found e.g., in *Current Protocols in Molecular Biology*, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. Conditions for hybridizations are largely dependent on the melting temperature Tm that is observed for half of the molecules of a substantially pure population of a double-stranded nucleic acid. Tm is the temperature in ° C. at which half the molecules of a given sequence are melted or single-stranded. For nucleic acids of sequence 11 to 23 bases, the Tm can be estimated in degrees C as 2(number of A+T residues)+4(number of C+G residues). Hybridization or annealing of nucleic acid molecules should be conducted at a temperature lower than the Tm, e.g., 15° C., 20° C., 25° C. or 30° C. lower than the Tm. The effect of salt concentration (in M of NaCl) can also be calculated. See, for example, Brown, A., "Hybridization" pp. 503-506, in *The Encyclopedia of Molec. Biol.*, J. Kendrew, Ed., Blackwell, Oxford (1994).

Preferably, the nucleic acid sequence of an efflux pump family member identified in this way is at least about 10%, 20%, more preferably at least about 30%, more preferably at least about 40% identical and preferably at least about 50%, or 60% identical to a query nucleotide sequence. In preferred embodiments, the nucleic acid sequence of a family member is at least about 70%, 80%, preferably at least about 90%, more preferably at least about 95% identical with a query nucleotide sequence. Preferably, family members have an amino acid sequence at least about 20%, preferably at least about 30%, more preferably at least about 40% identical and preferably at least about 50%, or 60% or more identical with a query amino acid sequence. In preferred embodiments, the nucleic acid sequence of a family member is at least about 70%, 80%, more preferably at least about 90%, or more preferably at least about 95% identical with a query nucleotide sequence.

However, it will be understood that the level of sequence similarity among microbial efflux pumps, even though members of the same family, is not necessarily high. This is particularly true in the case of divergent genomes where the level of sequence identity may be low, e.g., less than 20% (e.g., *B. burgdorferi* as compared e.g., to *B. subtilis*). Accordingly, structural similarity among efflux pump family members can also be determined based on "three-dimensional correspondence" of amino acid residues. As used herein, the language "three-dimensional correspondence" is meant to includes residues which spatially correspond, e.g., are in the same position of a known efflux pump family member as determined, e.g., by X-ray crystallography, but which may not correspond when aligned using a linear alignment program. The language "three-dimensional correspondence" also includes residues which perform the same function, e.g., bind to a specific substrate or associated molecule, as determined, e.g., by mutational analysis. Such analysis can be performed using comparison programs that are publicly available.

As used herein the term "efflux pump inhibitor" refers to a compound which interferes with the ability of an efflux pump to export a compound which it is normally capable of exporting in the absence of such an inhibitor. Such inhibitors can inhibit the activity of an efflux pump directly by blocking the pump, e.g., by binding at a substrate binding site and not being transported out of the cell. Inhibitors of efflux pumps can inhibit the growth of resistant or highly resistant microbes which used alone, or they may potentiate the activity of a drug to which the microbe is resistant. The inhibitor may have intrinsic antimicrobial (e.g., antibacterial) activity of its own, but at least a significant portion of the relevant activity is due to the efflux pump inhibiting activity. Of particular interest in this invention are compounds that inhibit the export or activity of efflux pumps which have a broad substrate range which includes antibacterial agents.

In one embodiment, an efflux pump inhibiting compound can be administered alone to inhibit the efflux of microbial waste products or environmental toxins. In another embodiment, an efflux pump blocking compound can be coadministered with a second agent, e.g., an antibiotic or a non-antibiotic agent. In one embodiment, the combination of an efflux pump blocking agent and the second agent is more effective than either the efflux pump blocking agent or the agent administered alone. Preferred second agents are substrates of the efflux pump.

The term "non-antibiotic agents" includes disinfectants, antiseptics, and surface delivered compounds. For example, antibiotics, biocides, or other type of antibacterial compounds, including agents which induce oxidative stress agents, and organic solvents are included in this term. The term "drug" also includes biocidal agents. The term "biocidal" is art recognized and includes an agent that those ordinarily skilled in the art prior to the present invention believed would kill a cell "non-specifically," or a broad spectrum agent whose mechanism of action is unknown, e.g., prior to the present invention, one of ordinary skill in the art would not have expected the agent to be target-specific. Examples of biocidal agents include paraben, chlorbutanol, phenol, alkylating agents such as ethylene oxide and formaldehyde, halides, mercurials and other heavy metals, detergents, acids, alkalis, and chlorhexidine. Other biocidal agents include triclosan, pine oil, quaternary amine compounds such as alkyl dimethyl benzyl ammonium chloride, chloroxylol, chlorhexidine, cyclohexidine, triclocarbon, and disinfectants. The term "bactericidal" refers to an agent that can kill a bacterium; "bacteriostatic" refers to an agent that inhibits the growth of a bacterium.

The term "antibiotic" is art recognized and includes antimicrobial agents synthesized by an organism in nature and isolated from this natural source, and chemically synthesized drugs. The term includes but is not limited to polyether ionophore such as monensin and nigericin; macrolide antibiotics such as erythromycin and tylosin; aminoglycoside antibiotics such as streptomycin and kanamycin; beta-lactam antibiotics such as penicillin and cephalosporin; and polypeptide antibiotics such as subtilisin and neosporin. Semi-synthetic derivatives of antibiotics, and antibiotics produced by chemical methods are also encompassed by this term. Chemically-derived antimicrobial agents such as isoniazid, trimethoprim, quinolones, fluoroquinolones and sulfa drugs are considered antibacterial drugs, and the term antibiotic includes these. Antibiotics also include peptide deformylase (PDF) inhibitors, such as actinonin, thiorphan, calpeptin, or other small molecules. (*J. Antimicrob. Chemother.* (2003) 51, 157-61). Additional examples of PDF inhibitors include the urea and hydroxamic acid compounds disclosed in U.S. patent application Ser. No. 2002/0119962, and these compounds are also antibiotics within the scope of the invention. Other exemplary antibiotics are illustrated elsewhere herein.

In contrast to the term "biocidal," an antibiotic or an "antimicrobial drug approved for human use" is considered to have a specific molecular target in a microbial cell. Preferably a microbial target of a therapeutic agent is sufficiently different from its physiological counterpart in a subject in need of treatment that the antibiotic or drug has minimal adverse effects on the subject.

The phrase "non-antibiotic agent" includes agents which are not art recognized as being antibiotics. Exemplary non-antibiotic agents include, e.g., biocides, disinfectants or anti-infectives. Non antibiotic agents also include agents which are incorporated into consumer goods, e.g., for topical use on a subject or as cleaning products. Non-antibiotic agents may be substrates of the efflux pump.

The prophylactic and therapeutic methods described herein can be used on susceptible or resistant organisms.

As used herein, the term "multiple drug resistance (MDR)" includes resistance to both antibiotic and non-antibiotic compounds. MDR results from the increased transcription of a chromosomal or plasmid encoded genetic locus in an organism, e.g., a marRAB locus, that results in the ability of the organism to minimize the toxic effects of a compound to which it has been exposed, as well as to other non-related compounds, e.g., by stimulating an efflux pump(s) or microbiological catabolic or metabolic processes.

As used herein, phrases like "microbes that are resistant to drugs or drug resistant microbes" includes microbes that are characterized by increased transcription of a genetic locus that affects drug resistance, e.g., an efflux pump gene. As used herein, the phrase "microbes which are resistant to drugs or drug resistant microbes" also includes microbes that are characterized by mutations in a gene that is the target of a drug.

As used herein, the phrase "microbes which are highly resistant to drugs or highly drug resistant microbes" includes microbes that are characterized by mutations in multiple (i.e., more than one) gene that affects drug resistance. Preferably, a microbe that is highly resistant to drugs is characterized by at least two of the following three traits: (1) it comprises at least one mutation in a gene encoding a drug target that renders the microbe resistant to one or more drugs (e.g., a gyrase, fabI, or topoisomerase mutation); (2) it comprises a second mutation (to the same gene or a different gene than in (1)) that increases drug resistance; and (3) it has increased expression of at least one efflux pump (e.g., as a result of increased transcription of the mar locus). The term "mutation" includes an alteration (e.g., a substitution, deletion, or insertion) of at least one nucleotide in the sequence of a nucleic acid molecule (either chromosomal or episomal) in a microbe which is capable of influencing drug resistance. Such a mutation can result, e.g., in altered gene regulation in the microbe or in the expression of an altered polypeptide. Preferably, such mutations are in genes which encode the target of the drug to which the microbe is resistant.

Microbes that are highly resistant to drugs are more resistant to drugs than microbes that that are characterized by only one of the preceding traits. In general, antibiotics, when tested for their effect on the growth of such highly resistant microbes, will yield a minimal inhibitory concentration (MIC) from between about 2-fold to more than 100-fold higher than that observed for a microbe that is characterized by only one of the above traits or a microbe that is multiply antibiotic resistant, but not highly resistant to drugs.

As used herein the term "growth" in reference to the growth of a microbe includes the reproduction or population expansion of the microbe, e.g., increase in numbers rather than increase in size. The term also includes maintenance of on-going metabolic processes of a microbe, e.g., those processes that keep the cell alive when the cell is not dividing.

As used herein, the term "infectivity" or "virulence" includes the ability of a pathogenic microbe to colonize a host, a first step required in order to establish growth in a host. Infectivity or virulence is required for a microbe to be a pathogen. In addition, a virulent microbe is one which can cause a severe infection. As used herein, the term "pathogen" includes both obligate and opportunistic organisms. The ability of a microbe to resist antibiotics is also important in promoting growth in a host, however, in one embodiment, antibiotic resistance is not included in the terms "infectivity" or "virulence" as used herein. Accordingly, in one embodiment, the instant invention pertains to methods of reducing the infectivity or virulence of a microbe without affecting (e.g., increasing or decreasing) antibiotic resistance. Preferably, as used herein, the term "infectivity or virulence" includes the ability of an organism to establish itself in a host by evading the host's barriers and immunologic defenses.

The inhibitors of efflux pumps for treating infections caused by a microbe may be a polyamine, e.g., a polyazaalkane, polyaminoalkane, or mixed poly(aza/amino)alkane. Any carbon atom of these compounds may be hydroxyl, amino, or oxo substituted. The inhibitor generally contains at least two nitrogen atoms that are bonded to a lipophilic group. For example, the inhibitor may be an aminoglycoside comprising at least two nitrogen atoms that are each bonded to a lipophilic group. Disclosed herein are several such inhibitors. Any novel compound including such inhibitors that is disclosed herein is within the scope of the present invention.

In certain embodiments, the term "substituted" means that the moiety has substituents placed on the moiety other than hydrogen which allow the molecule to perform its intended function. Examples of substituents include moieties selected from straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl (including benzyl), heteroaralkyl, alkylcarbonyl and arylcarbonyl or other such acyl group, heteroarylcarbonyl, or heteroaryl group, $(CR'R'')_{0-3}NR'R''$ (e.g., $-NH_2$), $(CR'R'')_{0-3}CN$ (e.g., $-CN$), $NO_2$, halogen (e.g., F, Cl, Br, or I), $(CR'R'')_{0-3}C(halogen)_3$ (e.g., $-CF_3$), $(CR'R'')_{0-3}CH(halogen)_2$, $(CR'R'')_{0-3}CH_2(halogen)$, $(CR'R'')_{0-3}CONR'R''$, $(CR'R'')_{0-3}(CNH)NR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-3}R'$ (e.g., $-SO_3H$), $(CR'R'')_{0-3}O(CR'R'')_{0-3}H$ (e.g., $-CH_2OCH_3$ and $-OCH_3$), $(CR'R'')_{0-3}S(CR'R'')_{0-3}H$ (e.g., $-SH$ and $-SCH_3$), $(CR'R'')_{0-3}OH$ (e.g., $-OH$), $(CR'R'')_{0-3}COR'$, $(CR'R'')_{0-3}$(substituted or unsubstituted phenyl), $(CR'R'')_{0-3}(C_3$-$C_8$ cycloalkyl), $(CR'R'')_{0-3}CO_2R'$(e.g., $-CO_2H$), or $(CR'R'')_{0-3}OR'$ group, wherein each of R' and R'' is independently hydrogen or a $C_1$-$C_5$ alkyl group.

In inhibitors of the invention, a "lipophilic group" generally will be a substituted or unsubstituted alkyl group. In one embodiment, the lipophilic group is a substituted benzyl group, e.g., $-CH_2$(substituted-phenyl). Benzyl groups may be conveniently added to a polyaminoalkane by reductive amination with the corresponding phenylaldehyde.

In more particular embodiments, the lipophilic group may be a substituted or unsubstituted N-benzyl group. For example, such N-benzyl groups may be substituted with one to five groups selected from $C_1$-$C_5$ straight or branched alkyl, $C_3$-$C_8$ cycloalkyl, $C_1$-$C_6$ alkoxy, $C_1$-$C_6$ thioalkyl, $C_2$-$C_6$ alkenyl, $C_2$-$C_6$ alkynyl, heterocyclic, carbocyclic, aryl, aryloxy, aralkyl, aryloxyalkyl, arylacetamidoyl, alkylaryl, heteroaralkyl, alkylcarbonyl, arylcarbonyl, heteroarylcarbonyl, heteroaryl group, $(CR'R'')_{0-3}NR'R''$, $(CR'R'')_{0-3}CN$, $NO_2$, halogen, $(CR'R'')_{0-3}C(halogen)_3$, $(CR'R'')_{0-3}CH(halogen)_2$, $(CR'R'')_{0-3}CH_2(halogen)$, $(CR'R'')_{0-3}CONR'R''$, $(CR'R'')_{0-3}(CNH)NR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-3}R'$, $(CR'R'')_{0-3}O(CR'R'')_{0-3}H$, $(CR'R'')_{0-3}S(CR'R'')_{0-3}H$, $(CR'R'')_{0-3}OH$, $(CR'R'')_{0-3}COR'$, $(CR'R'')_{0-3}$(substituted or unsubstituted phenyl), $(CR'R'')_{0-3}(C_3$-$C_8$ cycloalkyl), $(CR'R'')_{0-3}CO_2R'$, and $(CR'R'')_{0-3}OR'$ groups, wherein each of R' and R'' is independently hydrogen or a $C_1$-$C_5$ alkyl group.

The term "aminoglycosides" refers to organic molecules derived at least part from a saccharide or polysaccharide and having the empirical formula $C_mH_nN_pO_q$ (where m, n, p, and q are appropriate integers). For instance, the aminoglycosides are oligosaccharides consisting of an aminocyclohexanol moiety glycosidically linked to other amino sugars. Streptomycin, one of the best studied of the group, is produced by *Streptomyces griseus*. Streptomycin, and many other aminoglycosides, inhibits protein synthesis in the target organisms. "Carbohydrate" includes substituted and unsubstituted mono-, oligo-, and polysaccharides. Monosaccharides are simple sugars usually of the formula $C_6H_{12}O_6$ that may be linked to form oligosaccharides or polysaccharides. Monosaccharides include enantiomers and both the D and L stereoisomers of monosaccharides. Carbohydrates may have multiple anionic groups attached to each monosaccharide moiety. For example, in sucrose octasulfate, four sulfate groups are attached to each of the two monosaccharide moieties.

Generally, the inhibitors of the invention are small molecules. A "small molecule" refers to a compound which is not itself the product of gene transcription or translation (protein, RNA or DNA). Preferably a "small molecule" is a low molecular weight compound, e.g., less than 7500 amu, more preferably less 5000 amu and even more preferably less than 1000 amu.

The term "hydroxy" or "hydroxyl" includes the groups —H or —O (with an appropriate counter ion).

The term "amino" includes —$NH_2$ and substituted analogs thereof, which may be represented as —$NR_2$ or where NRH is the substituent.

The terms "aza" and "oxo" respectively refer to divalent nitrogen and oxygen atoms, e.g., the groups —NH— (and substituted analogs thereof, which may be represented as —NR— where R is the substituent) or —O—.

"Carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic group, preferably saturated. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2]bicyclooctane. A carbon atom may be substituted with a nitrogen or oxygen atom to produce an aza- or oxo-heterocycle. "Polycyclyl" or "polycyclic group" includes two or more cyclic rings (e.g., cycloalkyls, heterocyclyls) in which two or more carbons are common to two adjoining rings, e.g., the rings are "fused rings." Rings that are joined through non-adjacent atoms are termed "bridged" rings.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl, etc.), alkyl substituted cycloalkyl groups, and cycloalkyl substituted alkyl groups, and polycyclic alkyl groups including bicycloalkyl groups. The term alkyl may further include alkyl groups, which can further include oxygen or nitrogen atoms replacing one or more carbons of the hydrocarbon backbone (i.e., oxoalkanes and azaalkanes). An "alkylene" group is a divalent moiety derived from the corresponding alkyl group.

In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

The inhibitors of the invention are substituted polyamines, including polyazaalkanes, polyaminoalkanes, or mixed poly (aza/amino)alkanes, any carbon atom of which may be hydroxyl, amino, or oxo substituted, and wherein said inhibitor contains at least two nitrogen atoms that are bonded to a lipophilic group. Further examples include polyazaalkanes, polyazacycloalkanes, polyazapolycycloalkanes, polyaminoalkanes, polyaminocycloalkanes, polyaminopolycycloalkanes, polyazapolyaminoalkanes, polyazapolyaminocycloalkanes, polyazapolyaminopolycycloalkanes, any carbon atom of which may be hydroxyl, amino, or oxo substituted, wherein said inhibitor contains at least two nitrogen atoms that are bonded to a lipophilic group. Here, "poly" means "two or more." Nitrogen atoms may each have one or two lipophilic groups.

Inhibitors of the invention may be prepared from polyamines having chemically modifiable nitrogen atoms, e.g., aminoglycosides and other amine containing scaffolds that contain nitrogen atoms and carbon atoms, which may be substituted with oxygen atoms.

Further exemplary inhibitor compounds are within the following formula:

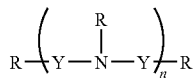

Formula I wherein each Y is independently —$(CX_2)_m$— (including a direct bond), —$(CX_2)_mO$— (including —O—), —$(CX_2)_m$NR—, $(CX_2)_mH$, —$(CX_2)_m$NHR, —$(CX_2)_m$OH, or two Y groups together form a ring structure, provided that a nitrogen/oxygen atom is not bonded to another nitrogen/oxygen atom, each R is independently a —H or a lipophilic group, each m is independently 0, 1, 2, 3, 4, 5, 6, 7, 8, 9, or 10, each n is independently is 2, 3, 4, 5, 6, 7, 8, 9, or 10, and each X is independently —H, —OH, or another Y group.

In another embodiment of Formula I, each Y is independently —$(CX_2)_m$— (including a direct bond), —$(CX_2)_mO$— (including —O—), —$(CX_2)_m$NR—, —$(CX_2)_mH$, —$(CX_2)_m$NHR, —$(CX_2)_m$OH, or two Y groups together form a ring structure, provided that a nitrogen/oxygen atom is not bonded to another nitrogen/oxygen atom, each R is independently a —H or a lipophilic group, each m is independently 0, 1, 2, 3, 4, 5, 6, 7, 8, 9, or 10, each n is independently is 2, 3, 4, 5, 6, 7, 8, 9, or 10, and each X is independently —$(CZ_2)_p$OH (including —OH), —$(CZ_2)_p$H (including —H), —$(CZ_2)_p$NH_2$ (including —$NH_2$), —$(CZ_2)_p$NHR, or two X groups together are —$(CZ_2)_p$—NR—$(CZ_2)_p$—, —$(CZ_2)_p$—, —$(CZ_2)_p$NR—, —O—$(CZ_2)_p$—, —$(CZ_2)_p$—O—$(CZ_2)_p$—, or a direct bond and both form a ring structure, each p is independently 0, 1, 2, 3, 4, 5, 6, 7, 8, 9, or 10, and each Z is independently —H, —OH, —$(CH_2)_2H$, —$(CH_2)_2H$, —$(CH_2)_2H$, —$NH_2$, or —NHR.

Another group of inhibitor compounds within the scope of the invention include those inhibitors having the following structure:

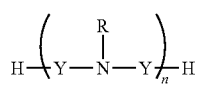

Formula II wherein each Y is independently —$(CX_2)_m$— (including a direct bond), —$(CX_2)_mO$— (including —O—), —$(CX_2)_m$NR—, —$(CX_2)_mH$, —$(CX_2)_m$NHR, —$(CX_2)_m$OH, or two Y groups together form a ring structure, provided that a nitrogen/oxygen atom is not bonded to another nitrogen/oxygen atom, each R is independently a —H or a lipophilic group, each m is independently 0, 1, 2, 3, 4, 5, 6, 7, 8, 9, or 10, each n is independently is 2, 3, 4, 5, 6, 7, 8, 9, or 10, and each X is independently —H, —OH, or another Y group.

In another embodiment of Formula II, each Y is independently —$(CX_2)_m$— (including a direct bond), —$(CX_2)_mO$— (including —O—), —$(CX_2)_m$NR—, —$(CX_2)_mH$, —$(CX_2)_m$NHR, —$(CX_2)_m$OH, or two Y groups together form a ring structure, provided that a nitrogen/oxygen atom is not bonded to another nitrogen/oxygen atom, each R is independently a —H or a lipophilic group, each m is independently 0, 1, 2, 3, 4, 5, 6, 7, 8, 9, or 10, each n is independently is 2, 3, 4, 5, 6, 7, 8, 9, or 10, and each X is independently —$(CZ_2)_p$OH (including —OH), —$(CZ_2)_p$H (including —H), —$(CZ_2)_p$NH_2$ (including —$NH_2$), —$(CZ_2)_p$NHR, or two X groups together are —(CZ$_2$)$_p$—NR—(CZ$_2$)$_p$—, —(CZ$_2$)$_p$—, —(CZ$_2$)$_p$NR—, —O—(CZ$_2$)$_p$—, —(CZ$_2$)$_p$—O—(CZ$_2$)$_p$—, or a direct bond and both form a ring structure, each p is independently 0, 1, 2, 3, 4, 5, 6, 7, 8, 9, or 10, and each Z is independently —H, —OH, —(CH$_2$)$_2$H, —(CH$_2$)$_2$H, —(CH$_2$)$_2$H, —NH$_2$, or —NHR.

Another embodiment of the invention includes inhibitors having the following structure:

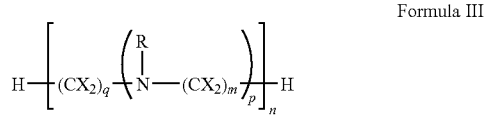

Formula III wherein each X is independently —(CZ$_2$)$_p$OH (including —OH), —(CZ$_2$)$_p$H (including —H), —(CZ$_2$)$_p$NH$_2$ (including —NH$_2$), —(CZ$_2$)$_p$NHR, or two X groups together are —(CZ$_2$)$_p$—NR—(CZ$_2$)$_p$—, —(CZ$_2$)$_p$—, —(CZ$_2$)$_p$NR—, —O—(CZ$_2$)$_p$—, —(CZ$_2$)$_p$—O—(CZ$_2$)$_p$—, or a direct bond and b form a ring structure, each R is independently a —H or a lipophilic group, each Z is independently —H, —OH, —(CH$_2$)$_2$H, —(CH$_2$)$_2$H, —(CH$_2$)$_2$H, —NH$_2$, or —NHR, each m is independently 0, 1, 2, 3, 4, 5, 6, 7, 8, 9, or 10, each n is independently 0, 1, 2, 3, 4, 5, 6, 7, 8, 9, or 10, each p is independently 0, 1, 2, 3, 4, 5, 6, 7, 8, 9, or 10, and each q is independently 0, 1, 2, 3, 4, 5, 6, 7, 8, 9, or 10, provided that p+n≧2.

Further examples of inhibitors have either of the following structures:

Formula IV

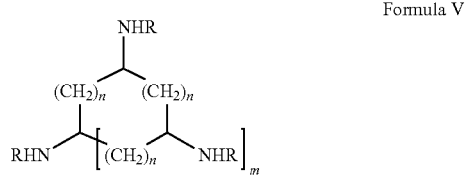

Formula V wherein each n is independently 1, 2, 3, 4, 5, 6, 7, 8, 9, or 10; m is 0, 1, 2, 3, 4, or 5; and each R is independently a —H or a lipophilic group.

It will be noted that the structures of some of the compounds of this invention include stereogenic carbon atoms. It is to be understood accordingly that the isomers arising from such asymmetry (e.g., all enantiomers and diastereomers) are included within the scope of this invention unless indicated otherwise. That is, unless otherwise stipulated, any chiral carbon center may be of either (R)- or (S)-stereochemistry. Such isomers can be obtained in substantially pure form by classical separation techniques and by stereochemically controlled synthesis.

The invention also pertains to any of the efflux blocking agents described herein.

The invention also relates to a method for treating a microbial infection or virulence in a subject, e.g., an animal or a plant or to methods of inhibiting microbial growth using compounds of the invention.

In one embodiment, an efflux pump inhibitor of the invention is administered alone to treat infection or virulence or to inhibit microbial growth. In another embodiment, the inhibitor is administered in combination with a second agent, e.g., a non-antibiotic or antibiotic drug as described herein.

In one embodiment, an efflux pump inhibitor is administered in an amount sufficient to reduce efflux pump activity.

Similarly, the invention embraces a method of treating an infection caused by a microbe in a subject comprising administering an inhibitor of an efflux pump that is a compound of the invention.

Additionally, the present invention includes a method of enhancing the antimicrobial activity of an antimicrobial agent against a microbe, which may be effluxed by a microbe, comprising contacting said microbe with said antimicrobial agent and an efflux pump inhibitor compound of the invention.

The term "microbe" includes any microorganism having an efflux pump. Preferably unicellular microbes including bacteria, fungi, or protozoa. In another embodiment, microbes suitable for use in the invention are multicellular, e.g., parasites or fungi. In preferred embodiments, microbes are pathogenic for humans, animals, or plants. As such, any of these disclosed microbes may be used as intact cells or as sources of materials for cell-free assays as described herein.

In the methods of the invention, the microbe may a bacterium. In methods of the invention, the bacterium to be inhibited through the use of an efflux pump inhibitor can be one of the following: *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophila, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, vibrio parahaemolyticus, Legionella pneumophila, Listeria monocytogenes, Neisseria gonorrhoeae, Neisseria meningitidis, Gardnerella vaginalis, Bacteroides fragilis, Bacteroides distasonis*, Bacteroides 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus interme-* dius, *Staphylococcus hyicus* subsp. *hyicus, Staphylococcus haemolyticus, Staphylococcus hominis, Staphylococcus saccharolyticus.*

In a preferred embodiment, the microbe is *Haemophilus influenzae*. In another embodiment, the compositions and methods of the invention are used to treat respiratory infection.

In another embodiment, an example of a microbe appropriate for the use of an efflux pump inhibitor is a pathogenic bacterial species, *Pseudomonas aeruginosa*, which is intrinsically resistant to many of the commonly used antibacterial agents. Exposing this bacterium to an efflux pump inhibitor can significantly slow the export of an antibacterial agent from the interior of the cell or the export of siderophores. Therefore, if another antibacterial agent is administered in conjunction with the efflux pump inhibitor, the antibacterial agent, which would otherwise be maintained at a very low intracellular concentration by the export process, can accumulate to a concentration which will inhibit the growth of the bacterial cells. This growth inhibition can be due to either bacteriostatic or bactericidal activity, depending on the specific antibacterial agent used. While *P. aeruginosa* is an example of an appropriate bacterium, other bacterial and microbial species may contain similar broad substrate pumps, which actively export a variety of antimicrobial agents, and thus can also be appropriate targets.

In addition as suggested above, for some microbial, e.g., bacterial, species, efflux pump inhibitors can decrease the virulence of the microbe, for example, by inhibiting the transport of factors important for pathogenicity. Again using *P. aeruginosa* as an example, inhibition of an efflux pump in this bacterium inhibits the uptake of iron, which is important for pathogenicity. The mechanism of bacterial iron transport involves molecules called siderophores, which are synthesized and exported by bacterial cells via efflux pumps. These siderophores bind tightly to iron scavenged from the host, and are then taken up by the bacteria. In this way, the iron needed for bacterial metabolism is obtained, and an infection can be maintained.

Similar pumps are found in other microorganisms. Some or all of the above effects can also be obtained with those microbes, and they are therefore also appropriate targets for detecting or using efflux pump inhibitors. Thus, the term "microbes" include, for example, bacteria, fungi, yeasts, and protozoa.

In another aspect, this invention provides a method for treating a microbial infection, e.g., a bacterial infection, in an animal by administering to an animal suffering from such an infection an efflux pump inhibitor as described above in an amount sufficient to reduce efflux pump activity.

In a preferred embodiment, the inhibitor is one which decreases the pathogenicity of the microbe. In preferred embodiments, microbes suitable for testing are bacteria from the family Enterobacteriaceae. In more preferred embodiments bacteria of a genus selected from the group consisting of *Escherichia, Proteus, Salmonella, Klebsiella, Providencia, Enterobacter, Burkholderia, Pseudomonas, Acinetobacter, Aeromonas, Haemophilus, Yersinia, Neisseria,* and *Erwinia, Rhodopseudomonas,* or *Burkholderia.* In yet other embodiments, the microbes to be tested are Gram-positive bacteria and are from a genus selected from the group consisting of *Lactobacillus, Azorhizobium, Streptococcus, Pediococcus, Photobacterium, Bacillus, Enterococcus, Staphylococcus, Clostridium, Butyrivibrio, Sphingomonas, Rhodococcus,* or *Streptomyces.* In yet other embodiments, the microbes to be tested are acid fast bacilli, e.g., from the genus *Mycobacterium*. In still other embodiments, the microbes to be tested are, e.g., selected from a genus selected from the group consisting of *Methanobacterium, Sulfolobus, Archaeoglobu, Rhodobacter,* or *Sinorhizobium.* In other embodiments, the microbes to be tested are fungi. In a preferred embodiment the fungus is from the genus *Mucor* or *Candida,* e.g., *Mucor racemosus* or *Candida albicans.*

In still another embodiment, the microbes are selected from *H. influenzae*, Gram-negative bacteria (e.g., *E. coli, P. aeruginosa, E. aerogenes, C. jejuni, Y enterocolitica, S. maltophilia*), and Gram-positive bacteria (e.g., *S. aureus, E. faecalis*). Still other examples include *V. parahaem* and *L. lactis*.

In yet other embodiments, the microbes to be tested are protozoa. In a preferred embodiment the microbe is a malaria or cryptosporidium parasite.

The methods of the invention are beneficially applied to a microbe that is a drug resistant microbe, or a highly drug resistant microbe, such as a microbe that is highly resistant to an antibiotic. In one embodiment, the microbial cell comprises at least one chromosomal mutation in a drug target gene, for example, a mutation is present in a gene selected from the group consisting of gyrase, topoisomerase, and fabI.

In medical applications, the inhibitor may be administered prophylacticly or therapeutically. In cases where the microbe is a drug resistant microbe, the drug to which the microbe is resistant may also administered to said subject along with the inhibitor. Accordingly, the inhibitor and drug may be administered as a pharmaceutical composition comprising said inhibitor, the drug, and a pharmaceutically acceptable carrier.

By way of example, in one embodiment, the drug is an antibiotic, e.g., cephalosporin, fluoroquinolone, macrolide, penicillin, or tetracycline antibiotic. Other exemplary antibiotics include: cephalosporins (cefaclor, cephalexin, Cefzil™, Omnicef™), fluoroquinolones (Avelox™, Cipro™, Levaquin™), macrolides (erythromycins, Biaxin™, Zithromax™), penicillins (amoxicillin, dicloxacillin, penicillin VK, Augmentin™), tetracyclines (doxycycline hyclate, Minocycline™, tetracycline), and others (metronidazole, sulfamethoxazole, trimethoprim). Similar antibiotic drugs include "Amoxil™ Capsules" (amoxicillin capsules, powder for oral suspension and chewable tablets), "Augmentin™" (amoxicillin/clavulanate potassium powder for oral suspension and chewable tablets), Augmentin™ (amoxicillin/clavulanate potassium tablets), "Bactroban™ Cream" (mupirocin calcium cream, 2%), "Bactroban™ Ointment" (mupirocin ointment, 2%), and "Bactroban™ Nasal" (mupirocin calcium ointment, 2%) all by SmithKline Beecham Pharmaceuticals; "Biaxin™ Filmtab Tablets" granules for oral suspension (clarithromycin) by Abbott Laboratories; "Ceftin™ Tablets" powder for oral suspension (cefuroxime axetil) by Glaxo Wellcome, Inc.; "Cipro™ Tablets" (ciproflaxacin hydrochloride) by Bayer Corporation; "Denavir™ Cream" (penciclovir cream) by SmithKline Beecham Pharmaceuticals; and "ERY-TAB™ Tablets" (erythromycin delayed-release tablets, USP) by Abbott Laboratories.

Also in particular embodiments various antibacterial drugs can be used. These include quinolones, tetracyclines, glycopeptides, aminoglycosides, beta-lactams, rifamycins, macrolides, oxazolidinones, coumermycins, and chloramphenicol. In particular embodiments an antibiotic of the above classes can be, for example, one of the following: beta-lactam antibiotics (imipenem, meropenem, biapenem, cefaclor, cefadroxil, cefamandole, cefatrizine, cefazedone, cefazolin, cefixime, cefinenoxime, cefodizime, cefonicid, cefoperazone, ceforanide, cefotaxime, cefotiam, cofpimizole, cefpiramide, cefpodoxime, cefsulodin, ceftazidime, cefteram, ceftezole, ceftibuten, ceftizoxime, ceftriaxone, cefuiroxime, cefuizonam, cephaacetrile, cephalexin, cephaloglycin, cephaloridine, cephalothin, cephapirin, cephradine, cefinetazole, cefoxitin, cefotetan, azthreonam, carumonam, flomoxef, moxalactam, amidinocillin, amoxicillin, ampicillin, azlocillin, carbenicillin, benzylpenicillin, carfecillin, cloxacillin, dicloxacillin, methicillin, mezlocillin, nafcillin, oxacillin, penicillin G, piperacillin, sulbenicillin, temocillin, ticarcillin, cefditoren, SC004, KY-020, cefdinir, ceftibuten, FK-312, S-1090, CP-0467, BK-218, FK-037, DQ-2556, FK-518, cefozopran, ME1228, KP-736, CP-6232, Ro 09-1227, OPC-20000, LY206763), macrolides (azithromycin, clarithromycin, erythromycin, oleandomycin, rokitamycin, rosaramicin, roxithromycin, troleandomycin), quinolones (amifloxacin, cinoxacin, ciprofloxacin, enoxacin, fleroxacin, flumequine, lomefloxacin, nalidixic acid, norfoxacin, ofloxacin, levofloxacin, oxolinic acid, pefloxacin, rosoxacin, temafloxacin, tosufloxacin, sparfioxacin, clinafloxacin, PD131628, PD138312, PD140248, Q-35, AM-1155, NM394, T-3761, rufloxacin, OPC-17116, DU-6859a (Sato, K. et al. (1992) *Antimicrob. Agents Chemother.* 37, 1491), DV-7751a (Tanaka, et al. (1992) *Antimicrob. Agents Chemother.* 37, 2212), tetracyclines and oxazolidinones (chlortetracyline, demeclocycline, doxycycline, lymecycline, methacycline, minocycline, oxytetracycline, tetracycline, linezolide, eperozolid), aminoglycosides (amikacin, arbekacin, butirosin, dibekacin, fortimicins, gentamicin, kanamycin, meomycin, netilmicin, ribostamycin, sisomicin, spectinomycin, streptonycin, tobramycin, clindamycin, lincomycin), and oxazolidinones (Linezolid(U-100766), eperezolide(U-100592)). Each of the above compounds have been reported in the literature. Other antibiotic compounds which may be identified which are effuxed by particular bacteria can also be utilized with the efflux pump inhibitors of this invention.

In another embodiment, the drug is a peptide deformylase inhibitors, such as actinonin, thiorphan, calpeptin, or other small molecules. (*J. Antimicrob. Chemother.* (2003) 51, 157-61; see also, U.S. Patent Application no. 2002/0119962).

In one embodiment, rather than coadministering an efflux pump inhibitor and a second agent, the efflux pump inhibitor and the second agent can be joined, e.g., using a linkage such as a covalent linkage, to form one bifunctional molecule.

In another embodiment, the invention relates to a method of enhancing the antimicrobial activity of a drug comprising contacting a microbe that is resistant to one or more drugs with a drug to which the microbe is resistant and an inhibitor compound of the invention that is an inhibitor of an efflux pump to thereby enhance the antimicrobial activity of a drug. The step of contacting may occur ex vivo.

The invention also relates to a pharmaceutical composition for use in the methods of the invention. In one such embodiment, the invention relates to a pharmaceutical composition effective for treatment of an infection of an animal by a microbe, comprising an efflux pump inhibitor compound of the invention and a pharmaceutically acceptable carrier.

In another aspect, the invention relates to a composition comprising a non-antibiotic bactericidal or bacteriostatic first agent and a second agent that inhibits the expression or activity of an efflux pump, wherein said inhibitor is a compound of the invention. For example, the second agent may be an inhibitor compound of the invention, such as N-benzylated polyazaalkanes, N-benzylated polyaminoalkanes, or mixed N-benzylated poly(aza/amino)alkanes, any carbon atom of which may be hydroxyl, amino, or oxo substituted. As another example, the second agent may inhibit an acr-like efflux pump.

Furthermore, the invention pertains to a pharmaceutical composition comprising an antibiotic and an inhibitor of an efflux pump selected from the group consisting of N-benzylated polyazaalkanes, N-benzylated polyaminoalkanes, or mixed N-benzylated poly(aza/amino)alkanes, any carbon atom of which may be hydroxyl, amino, or oxo substituted. Such pharmaceutical compositions may further comprise a pharmaceutically acceptable carrier, which itself may be an inhibitor of the pump. Many antibiotics may be used in such compositions, such as a cephalosporin, fluoroquinolone, macrolide, penicillin, or tetracycline antibiotic.

The present invention also relates to a method of treating an infection caused by a microbe in a subject comprising administering an inhibitor of an efflux pump according to the invention to the subject such that the infection is treated.

Likewise, the present invention relates to a method of enhancing the antimicrobial activity of a drug comprising contacting a microbe that is resistant to one or more drugs with a drug to which the microbe is resistant and an inhibitor of an efflux pump according to the invention to thereby enhance the antimicrobial activity of a drug.

In another aspect the invention pertains to methods of enhancing the antimicrobial activity of a drug by contacting a microbe that is resistant to one or more drugs with a drug to which the microbe is resistant and an inhibitor of an efflux pump. In one embodiment, the microbe is contacted with the drug and the inhibitor of the efflux pump ex vivo. This method can be used, e.g., in disinfecting surfaces to prevent the spread of infection or in cleaning surfaces which are fouled by microbial growth. Preferably, the drug used to contact the microbe is a non-antibiotic drug. In a preferred embodiment, the microbe is contacted with triclosan and an inhibitor of an efflux pump.

In one embodiment, an efflux pump inhibitor and a drug can be combined in a disinfectant, e.g., a cleaning product or a household product for contacting with resistant microbes. Exemplary cleaning products can be used topically on a subject (e.g., as soaps or lotions) or can be used for cleaning surfaces. In one embodiment, an efflux pump inhibitor is itself a disinfectant.

This method is useful, for example, to prevent or cure contamination of a cell culture by a bacterium possessing an efflux pump. However, it applies to any situation where such growth suppression is desirable.

In a further related aspect, this invention includes a method for prophylactic treatment of a mammal. In this method, an antimicrobial agent and an efflux pump inhibitor is administered to a mammal at risk of a microbial infection, e.g., a bacterial infection.

In the context of the response of a microbe, such as a bacterium, to an anti-microbial agent, the term "susceptibility" refers to the sensitivity of the microbe for the presence of the antimicrobial agent. So, to increase the susceptibility means that the microbe will be inhibited by a lower concentration of the antimicrobial agent in the medium surrounding the microbial cells. This is equivalent to saying that the microbe is more sensitive to the antimicrobial agent. In most cases the minimum inhibitory concentration (MIC) of that antimicrobial agent will have been reduced.

According to the invention, "inhibitor of an efflux pump" includes substituted polyamines, including substituted aminoglycosides. Polyamines have at least two amino groups. In some embodiments, inhibitors of the invention have greater than 4 amino groups, or greater than 6 amino groups, or more.

In one aspect the invention provides a method of treating an infection, e.g., a drug resistant infection, in a subject comprising administering a drug (e.g., to which a microbe is resistant) and an inhibitor of an efflux pump to the subject. As used herein the term "administration" includes contacting a compound (e.g., an inhibitor of an efflux pump) with a microbe, e.g. in vivo or in vitro. Thus, an efflux pump inhibitor and a drug can be administered for in vivo treatment or can be used topically, e.g., on skin or the eyes.

In one embodiment, the drug is an antibiotic, e.g., a fluoroquinolone. In another embodiment, the drug is a non-antibiotic composition, e.g., triclosan. In another embodiment the infection to be treated is one normally treated with an antibiotic composition. In another embodiment, the infection to be treated is not one normally treated with a non-antibiotic composition.

In one embodiment of the treatment method, the efflux pump inhibitor and the drug are administered separately to the subject. In another embodiment, the efflux pump inhibitor and the drug are administered simultaneously. In one embodiment, the simultaneous administration of the drug and the efflux pump inhibitor is facilitated by the administration of a pharmaceutical composition comprising both an efflux pump inhibitor and a drug to which the microbe is resistant.

The amount of efflux pump inhibitor to be administered to a subject is a therapeutically effective amount, e.g., for an efflux pump inhibitor, an amount sufficient to reduce efflux pump activity. The dosage of efflux pump inhibitor to be administered to a subject that would benefit from treatment with a drug, e.g. a patient having an infection with a microbe, can readily be determined by one of ordinary skill in the art. Ideally, the dosage of efflux pump inhibitor administered will be sufficient to reduce efflux pump activity such that standard doses of drugs have a therapeutic effect, e.g., result in a benefit to the subject, e.g., by inhibiting microbial growth. The phrase "therapeutic effect" refers to an amelioration of symptoms or a prolongation of survival in a subject. In a preferred embodiment, a therapeutic effect is an elimination of a microbial infection.

The compounds of the invention are useful in agricultural, veterinary and clinical applications. In one embodiment, the subject is an avian subject, e.g., a chicken or a turkey. In another embodiment, the subject is a mammalian subject, e.g., a horse, sheep, pig, cow, dog, cat, or a human. In a preferred embodiment, the subject is a human subject. In another embodiment, the subject is a plant.

In yet another aspect, this invention provides a method for enhancing growth of an animal by administering an efflux pump inhibitor to the animal, which inhibits an efflux pump expressed in a bacterial strain in the animal, and which inhibits the growth of that bacterial strain. Such a growth enhancing effect may result from the reduced energy consumption by the bacteria, which increases the food energy available to the animal. This method is appropriate, for example, for use with cattle, swine, and fowl such as chickens and turkeys In one embodiment, the microbe is resistant to one or more drugs. In a preferred embodiment, the microbe is highly resistant to one or more drugs. In one embodiment, the drug is an antibiotic. In another embodiment, the drug is a non-antibiotic. In another embodiment, the drug is triclosan. In one embodiment, a microbe comprises a mutation in a gene which is a target of the drug to which the microbe is resistant, e.g., topoisomerase, gyrase, orfabi gene. In another embodiment, a microbe comprises a mutation in at least two of a topoisomerase, gyrase, orfabi gene.

In a related aspect, this invention provides a method of treating an animal suffering from a microbial infection by administering to the animal an efflux pump inhibitor in an amount sufficient to reduce efflux pump activity. In this aspect, the efflux pump inhibitor is one which reduces the in vivo viability of a microbe involved in the infection. By reducing the in vivo viability, the infected animal can more readily clear its body of the infection, or the microbes may even be killed. In particular embodiments the animal is a mammal. Also in particular embodiments, the microbe may be from one of a variety of pathogenic bacterial species, specifically including those listed above.

In one embodiment, an infection in a subject is treated prophylacticly. The term "prophylactic" treatment refers to treating a subject who is not yet infected, but who is susceptible to, or at risk of an infection. In one embodiment, the efflux pump inhibitor is administered prior to exposure to an infectious agent. In another embodiment, an efflux pump inhibitor is administered to a subject prior to the exposure of the subject to a drug resistant organism. The term "therapeutic" treatment refers to administering a compound to a subject already suffering from an infection.

In one embodiment an efflux pump inhibitor or drug may be administered in prodrug form, e.g., may be administered in a form which is modified within the cell to produce the functional form of the efflux pump inhibitor. Prodrugs are compounds which are converted in vivo to active forms. Prodrugs can be used to alter the biodistribution (e.g., to allow compounds which would not typically enter the reactive site of the protease) or the pharmacokinetics for a particular compound. See, e.g., R. B. Silverman (1992) "The Organic Chemistry of Drug Design and Drug Action," Academic Press, Chp. 8. For example, a carboxylic acid group, can be esterified, e.g., with a methyl group or an ethyl group to yield an ester. When the ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate compound which subsequently decomposes to yield the active compound. The prodrug moieties may be metabolized in vivo by esterases or by other mechanisms to carboxylic acids. The prodrugs can be prepared in situ during the final isolation and purification of the compounds, or by separately reacting the purified compound in its free acid form with a suitable derivatizing agent. Carboxylic acids can be converted into esters via treatment with an alcohol in the presence of a catalyst. Examples of cleavable carboxylic acid prodrug moieties include substituted and unsubstituted, branched or unbranched lower alkyl ester moieties, (e.g., ethyl esters, propyl esters, butyl esters, pentyl esters, cyclopentyl esters, hexyl esters, cyclohexyl esters), lower alkenyl esters, dilower alkyl-amino lower-alkyl esters (e.g., dimethylaminoethyl ester), acylamino lower alkyl esters, acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, dilower alkyl amides, and hydroxy amides.

Toxicity and therapeutic efficacy of Inhibitor compounds can be determined by standard pharmaceutical procedures in cell cultures or experimental animals, e.g., for determining the LD50 (the dose lethal for 50% of the population) and the ED50 (the does therapeutically effective in 50% of the population). The dose ratio between toxic and therapeutic effects is the therapeutic index and it can be expressed as the ratio between LD50/ED50. Compounds which exhibit large therapeutic indices are preferred. The data obtained from these cell culture assays and animal studies can be used in formulating a range of dosage for use in human subjects. The dosage of such compounds lies preferably within a range of circulating concentrations that include the ED50 with little or no toxicity.

The dosage may vary within this range depending upon the dosage form employed and the route of administration utilized. For example, in one embodiment the therapeutic serum concentration of an efflux pump inhibitor is in the range of 0.1-100 μg/ml.

The invention provides pharmaceutically acceptable compositions which include a therapeutically-effective amount or dose of an efflux pump inhibitor and one or more pharmaceutically acceptable carriers (additives) or diluents. A composition can also include a second antimicrobial agent, e.g., an antimicrobial compound, preferably an antibiotic, e.g., a fluoroquinolone.

As described in detail below, the pharmaceutical compositions can be formulated for administration in solid or liquid form, including those adapted for the following (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream, foam, or suppository; or (5) aerosol, for example, as an aqueous aerosol, liposomal preparation or solid particles containing the compound.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the antimicrobial agents or compounds of the invention from one organ, or portion of the body, to another organ, or portion of the body without affecting its biological effect. Each carrier should be "acceptable" in the sense of being compatible with the other ingredients of the composition and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical compositions. Proper fluidity can be maintained, for example, by the use of coating materials, such as lecithin, by the maintenance of the required particle size in the case of dispersions, and by the use of surfactants.

A "carrier" or "excipient" is a compound or material used to facilitate administration of the compound, for example, to increase the solubility of the compound. Solid carriers include, e.g., starch, lactose, dicalcium phosphate, sucrose, and kaolin. Liquid carriers include, e.g., sterile water, saline, buffers, nonionic surfactants, and edible oils such as oil, peanut and sesame oils. In addition, various adjuvants such as are commonly used in the art may be included. These and other such compounds are described in the literature, e.g. in the Merck Index, Merck & Company, Rahway, N.J. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press.

In yet another aspect, the invention provides a method of suppressing growth of a microbe, e.g., a bacterium, expressing an efflux pump, e.g., a non-tetracycline-specific efflux pump.

These compositions may also contain additional agents, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Pharmaceutical compositions of the present invention may be administered to epithelial surfaces of the body orally, parenterally, topically, rectally, nasally, intravaginally, intracisternally. They are of course given by forms suitable for each administration route. For example, they are administered in tablets or capsule form, by injection, inhalation, eye lotion, ointment, etc., administration by injection, infusion or inhalation; topical by lotion or ointment; and rectal or vaginal suppositories.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a sucrose octasulfate or an antibacterial or a contraceptive agent, drug or other material other than directly into the central nervous system, such that it enters the subject's system and, thus, is subject to metabolism and other like processes, for example, subcutaneous administration.

In some methods, the compositions of the invention can be topically administered to any epithelial surface. An "epithelial surface" according to this invention is defined as an area of tissue that covers external surfaces of a body, or which and lines hollow structures including, but not limited to, cutaneous and mucosal surfaces. Such epithelial surfaces include oral, pharyngeal, esophageal, pulmonary, ocular, aural, nasal, buccal, lingual, vaginal, cervical, genitourinary, alimentary, and anorectal surfaces.

Compositions can be formulated in a variety of conventional forms employed for topical administration. These include, for example, semi-solid and liquid dosage forms, such as liquid solutions or suspensions, suppositories, douches, enemas, gels, creams, emulsions, lotions, slurries, powders, sprays, lipsticks, foams, pastes, toothpastes, ointments, salves, balms, douches, drops, troches, chewing gums, lozenges, mouthwashes, rinses.

Conventionally used carriers for topical applications include pectin, gelatin and derivatives thereof, polylactic acid or polyglycolic acid polymers or copolymers thereof, cellulose derivatives such as methyl cellulose, carboxymethyl cellulose, or oxidized cellulose, guar gum, acacia gum, karaya gum, tragacanth gum, bentonite, agar, carbomer, bladderwrack, ceratonia, dextran and derivatives thereof, ghatti gum, hectorite, ispaghula husk, polyvinypyrrolidone, silica and derivatives thereof, xanthan gum, kaolin, talc, starch and derivatives thereof, paraf fin, water, vegetable and animal oils, polyethylene, polyethylene oxide, polyethylene glycol, polypropylene glycol, glycerol, ethanol, propanol, propylene glycol (glycols, alcohols), fixed oils, sodium, potassium, aluminum, magnesium or calcium salts (such as chloride, carbonate, bicarbonate, citrate, gluconate, lactate, acetate, gluceptate or tartrate).

Such compositions can be particularly useful, for example, for treatment or prevention of an unwanted cell, e.g., vaginal Neisseria gonorrhea, or infections of the oral cavity, including cold sores, infections of eye, the skin, or the lower intestinal tract. Standard composition strategies for topical agents can be applied to the antimicrobial compounds, or pharmaceutically acceptable salts thereof in order to enhance the persistence and residence time of the drug, and to improve the prophylactic efficacy achieved.

For topical application to be used in the lower intestinal tract or vaginally, a rectal suppository, a suitable enema, a gel, an ointment, a solution, a suspension or an insert can be used. Topical transdermal patches may also be used. Transdermal patches have the added advantage of providing controlled delivery of the compositions of the invention to the body. Such dosage forms can be made by dissolving or dispersing the agent in the proper medium.

Compositions of the invention can be administered in the form of suppositories for rectal or vaginal administration. These can be prepared by mixing the agent with a suitable non-irritating carrier which is solid at room temperature but liquid at rectal temperature and therefore will melt in the rectum or vagina to release the drug. Such materials include cocoa butter, beeswax, polyethylene glycols, a suppository wax or a salicylate, and which is solid at room temperature, but liquid at body temperature and, therefore, will melt in the rectum or vaginal cavity and release the active agent.

Compositions which are suitable for vaginal administration also include pessaries, tampons, creams, gels, pastes, foams, films, or spray compositions containing such carriers as are known in the art to be appropriate. The carrier employed in the sucrose octasulfate/contraceptive agent should be compatible with vaginal administration or coating of contraceptive devices. Combinations can be in solid, semi-solid and liquid dosage forms, such as diaphragm, jelly, douches, foams, films, ointments, creams, balms, gels, salves, pastes, slurries, vaginal suppositories, sexual lubricants, and coatings for devices, such as condoms, contraceptive sponges, cervical caps and diaphragms.

For ophthalmic applications, the pharmaceutical compositions can be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the compositions can be formulated in an ointment such as petrolium. Exemplary ophthalmic compositions include eye ointments, powders, solutions and the like.

Powders and sprays can contain, in addition to sucrose octasulfate or antibiotic or contraceptive agent(s), carriers such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Compositions of the invention can also be orally administered in any orally-acceptable dosage form including, but not limited to, capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) or as mouth washes and the like, each containing a predetermined amount of sucrose octasulfate or antibiotic or contraceptive agent(s) as an active ingredient. A compound may also be administered as a bolus, electuary or paste. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Tablets, and other solid dosage forms, such as dragees, capsules, pills and granules, may be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the antimicrobial agent(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Sterile injectable forms of the compositions of this invention can be aqueous or oleaginous suspensions. These suspensions may be formulated according to techniques known in the art using suitable dispersing or wetting agents and suspending agents. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

The sterile injectable preparation may also be a sterile injectable solution or suspension in a nontoxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

Certain embodiments of the present compounds can contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed.

Representative salts include the hydrohalide (including hydrobromide and hydrochloride), sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, 2-hydroxyethylsulfonate, and laurylsulphonate salts and the like. (see, e.g., Berge et al. (1977) "Pharmaceutical Salts", *J. Pharm. Sci.* 66, 1-19).

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention.

These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

As used herein, "pharmaceutically acceptable carrier" includes appropriate solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, it can be used in the therapeutic compositions. Supplementary active ingredients can also be incorporated into the compositions.

With respect to in vivo applications, the formulations of the present invention can be administered to a patient in a variety of forms adapted to the chosen route of administration, namely, parenterally, orally, or intraperitoneally. Parenteral administration, which is preferred, includes administration by the following routes: intravenous; intramuscular; interstitially; intraarterially; subcutaneous; intra ocular; intrasynovial; trans epithelial, including transdermal; pulmonary via inhalation; ophthalmic; sublingual and buccal; topically, including ophthalmic; dermal; ocular; rectal; and nasal inhalation via insufflation. Intravenous administration is preferred among the routes of parenteral administration.

Pharmaceutical preparations for parenteral administration include aqueous solutions of the active compounds in water-soluble or water-dispersible form. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, or dextran, optionally, the suspension may also contain stabilizers.

Drug delivery vehicles can be chosen e.g., for in vitro, for systemic, or for topical administration. These vehicles can be designed to serve as a slow release reservoir or to deliver their contents directly to the target cell. An advantage of using some direct delivery drug vehicles is that multiple molecules are delivered per uptake. Such vehicles have been shown to increase the circulation half-life of drugs that would otherwise be rapidly cleared from the blood stream. Some examples of such specialized drug delivery vehicles which fall into this category are liposomes, hydrogels, cyclodextrins, biodegradable nanocapsules, and bioadhesive microspheres.

For prophylactic applications, the pharmaceutical composition of the invention can be applied prior to physical contact with a microbe. The timing of application prior to physical contact can be optimized to maximize the prophylactic effectiveness of the compound. The timing of application will vary depending on the mode of administration, the epithelial surface to which it is applied, the surface area, doses, the stability and effectiveness of composition under the pH of the epithelial surface, the frequency of application, e.g., single application or multiple applications. Preferably, the timing of application can be determined such that a single application of composition is sufficient. One skilled in the art will be able to determine the most appropriate time interval required to maximize prophylactic effectiveness of the compound.

One of ordinary skill in the art can determine and prescribe the effective amount of the pharmaceutical composition required. For example, one could start doses at levels lower than that required in order to achieve the desired therapeutic effect and gradually increase the dosage until the desired effect is achieved. In general, a suitable daily dose of a composition of the invention will be that amount of the composition which is the lowest dose effective to produce a therapeutic effect. Such an effective dose will generally depend upon the factors described above. It is preferred that administration be intravenous, intracoronary, intramuscular, intraperitoneal, or subcutaneous.

The practice of the present invention will employ, unless otherwise indicated, conventional techniques of cell biology, cell culture, molecular biology, genetics, microbiology, recombinant DNA, and immunology, which are within the skill of the art. Such techniques are explained fully in the literature. See, for example, "Genetics; Molecular Cloning A Laboratory Manual," 2nd Ed., ed. by Sambrook, J. et al. (Cold Spring Harbor Laboratory Press (1939)); "Short Protocols in Molecular Biology," 3rd Ed., ed. by Ausubel, F. et al. (Wiley, N.Y. (1995)); "DNA Cloning, Volumes I and II" (D. N. Glover ed., 1985); "Oligonucleotide Synthesis" (M. J. Gait ed. (1984)); Mullis et al. U.S. Pat. No. 4,633,195; "Nucleic Acid Hybridization" (B. D. Hames & S. J. Higgins eds. (1984)); the treatise, "Methods In Enzymology" (Academic Press, Inc., N.Y.); "Immunochemical Methods In Cell And Molecular Biology" (Mayer and Walker, eds., Academic Press, London (1987)); "Handbook of Experimental Immunology," Volumes I-IV (D. M. Weir and C. C. Blackwell, eds. (1986)); and Miller, J. "Experiments in Molecular Genetics" (Cold Spring Harbor Press, Cold Spring Harbor, N.Y. (1972)).

The invention is further illustrated by the following examples, which should not be construed as further limiting.

EXAMPLES

Example 1

Preparation of Substituted Polyamines

In general, polyamines may be derivatized using by, e.g., reductive amination with aryl aldehydes. Suitable polyamines include spermidine, spermine, norspermidine, spergaulin, 1,3,5-triamimocyclohexane, agrbactin, acyria pigments, and other products possessing 2 or more chemically modifiable amines. The polyamine substitution pattern may reside on one, two or three or more ring systems interconnected and in any pattern in a 3-D array.

For example, paromomycin derivatives (FIG. 2 and Table 2) are aminoglycosides possessing five primary amino functional groups (FIG. 1 and Table 1) and were produced by 5-N-benzylation using unsubstituted or substituted benzaldehydes under reduction by sodium borohydride. Many of these polysubstituted paromomycins are substrates of the efflux system of Haemophilus influenzae (Table 3) and act in synergy with tetracycline, doxycycline, and gentamicin to increase antibiotic susceptibility in H. influenzae (Table 4).

5-N-alkylation of paromomycin produced compounds lacking synergistic activity against the same strains indicating that the steric and lipophilic properties of the 5-N-benzylated compounds are required for optimal inhibitory activity.

The family of aminoglycosides and aminoglycoside substructures and the like may likewise be used to produce compounds of inhibitory activity.

TABLE 1

Substituents on various aminoglycoside antibiotics.

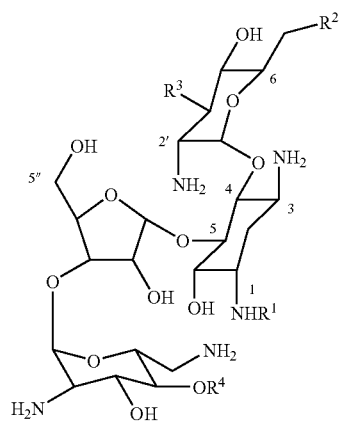

Core aminoglycoside scaffold.

| Aminoglycoside | $R^1$ | $R^2$ | $R^3$ | $R^4$ |
|---|---|---|---|---|
| Neomycin B | H | $NH_2$ | OH | H |
| Paromomycin I | H | OH | OH | H |

TABLE 2

Substitutents on various polysubstituted paromomycins.

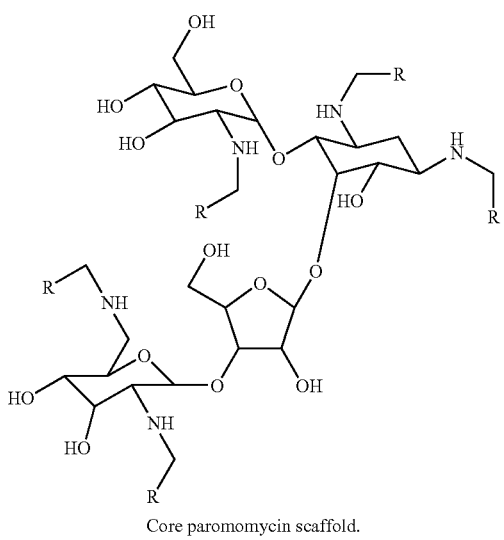

Core paromomycin scaffold.

| Substituted paromomycin | Code No. | R group |
|---|---|---|
| Methyl | G | $CH_3$ |
|  | K |  |
| Ethyl | E | $CH_2CH_3$ |
| Butyl | I | $(CH_2)_3CH_3$ |
| Isopentyl | C | $(CH_2)_2CH(CH_3)_2$ |

TABLE 2-continued

Substitutents on various polysubstituted paromomycins.

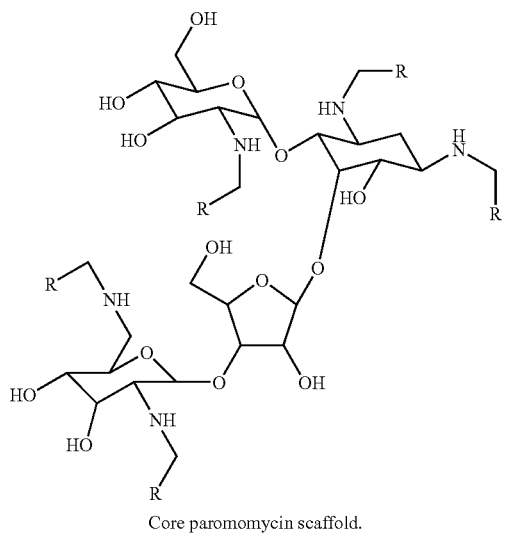

Core paromomycin scaffold.

| Substituted paromomycin | Code No. | R group |
|---|---|---|
| Nonyl | F<br>L | $(CH_2)_8CH_3$ |
| Benzyl | H | phenyl |
| Phenethyl | B | -CH2-phenyl |
| 2'-Cl Benzyl | A<br>J | 2-Cl-phenyl |
| Pyridylmethyl | M | pyridyl |

Example 2

Susceptibility of *Haemophilus Influenzae* to Various Paromomycin Derivatives AcrAB deleted strains of *H. influenzae* were constructed (see, e.g., Provence, D. L. and R. Curtiss III. (1994) In P. Gerhardt, R. G. E. Murray, W. A. Wood, and N. R. Krieg. (ed.), "Methods for General and Molecular Bacteriology," American Society for Microbiology, Washington. pp. 317-347). Deletion of acrAB was confirmed by the absence of intact target DNA in a PCR assay.

MICs of selected antimicrobial agents were determined by a standard broth microdilution procedure with cation adjusted Mueller Hinton broth (Becton Dickinson, Cockeysville, Md.) and an inoculum of 5×105 CFU/ml according to NCCLS performance and interpretive guidelines (NCCLS. 1997. Methods for dilution antimicrobial susceptibility. Tests for bacteria that grow aerobically, Fourth Edition; Approved Standard. NCCLS document M7 A4 (ISBN 1 56238 309 4). NCCLS, 940 West Valley Road, Suite 1400, Wayne, Pa. 19087). Antimicrobial agents tested included tetracycline, doxycycline, and gentamicin.

Table 3 shows the susceptibility of *H. influenzae* to various paromomycin derivatives. The acr deleted strain was more sensitive to the compounds than was the wild-type strain.

TABLE 3

Susceptibility of Huemophilus influenzae to various paromomycin derivatives.

| Host | Genotype | A | B | H | J |
|---|---|---|---|---|---|
| KW2O | wild type | >64 | 32 | >64 | >64 |
| KW2O -acr | -acr | 2 | 16 | 16 | 4 |

The susceptibility of *H. influenzae* to various antibiotics was tested in the presence of a polysubstituted paromomycin. Increased susceptibility of the organism to the antibiotics was observed in 7 out of the 9 combinations tested.

TABLE 4

Susceptibility of Haemophilus influenzae to various antibiotics in the presence of A (a polysubstituted paromomycin).

| Host | Genotype | tetracycline | doxycycline | gentamicin |
|---|---|---|---|---|
| KW20 | wild type, lab isolate | + | − | + |
| 8 | clinical isolate | + | + | + |
| 15 | clinical isolate | − | + | + |

"+" = increased susceptibility to the indicated antibiotic was observed in the presence of a polysubstituted paromomycin (A); "−" = an increase in susceptibility the indicated antibiotic was not observed in the presence of a polysubstituted paromomycin (A)

INCORPORATION BY REFERENCE

The entire contents of all patents, published patent applications and other references cited herein are hereby expressly incorporated herein in their entireties by reference.

EQUIVALENTS

Those skilled in the art will recognize, or be able to ascertain using no more than routine experimentation, numerous equivalents to the specific procedures described herein. Such equivalents are considered to be within the scope of this invention and are covered by the following claims.

The invention claimed is:

1. An efflux inhibitor, wherein said inhibitor comprises the structure

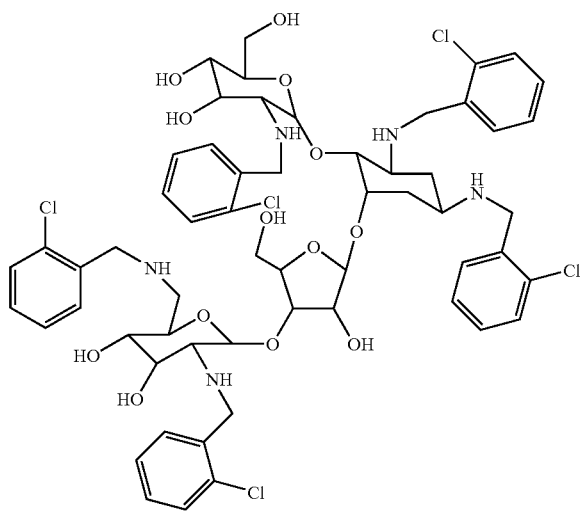

and pharmaceutically acceptable salts thereof.

2. An efflux pump inhibitor of formula I:

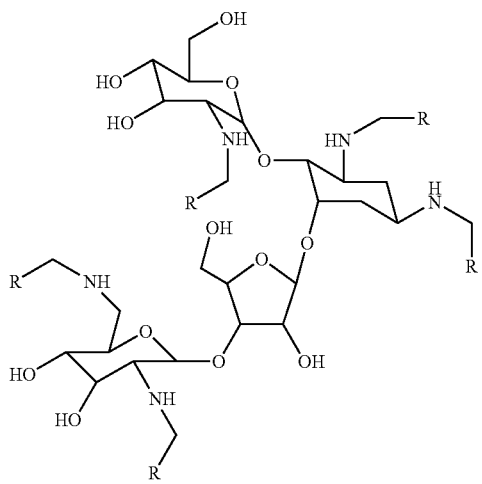

wherein R is methyl, ethyl, butyl, isopentyl, nonyl, benzyl, phenethyl, 2'-Cl-benzyl or pyridylmethyl; and pharmaceutically acceptable salts thereof.

3. A pharmaceutical composition comprising the efflux pump inhibitor of claim 1 and a pharmaceutically acceptable carrier.

4. A pharmaceutical composition comprising the efflux pump inhibitor of claim 2 and a pharmaceutically acceptable carrier.

5. A pharmaceutical composition comprising a non-antibiotic bactericidal or bacteriostatic first agent and the efflux inhibitor of claim 1.

6. The composition of claim 5, wherein said first agent is an antibiotic.

7. The composition of claim 5, wherein the efflux inhibitor inhibits an acr-like efflux pump.

8. The composition of claim 5, further comprising a pharmaceutically acceptable carrier.

9. A composition comprising a non-antibiotic bactericidal or bacteriostatic first agent and the efflux inhibitor of claim 2.

10. The composition of claim 9, wherein said first agent is an antibiotic.

11. The composition of claim 9, wherein the efflux pump inhibitor inhibits an acr-like efflux pump.

12. The composition of claim 9, further comprising a pharmaceutically acceptable carrier.

13. A pharmaceutical composition comprising an antibiotic and the efflux pump inhibitor of claim 1.

14. The composition of claim 13, further comprising a pharmaceutically acceptable carrier.

15. The composition of claim 13, wherein the antibiotic is a peptide deformylase inhibitor.

16. The composition of claim 14, wherein the pharmaceutically acceptable carrier is an inhibitor of said efflux pump.

17. A pharmaceutical composition comprising an antibiotic and the efflux pump inhibitor of claim 2.

18. The composition of claim 17, further comprising a pharmaceutically acceptable carrier.

19. The composition of claim 17, wherein the antibiotic is a peptide deformylase inhibitor.

20. The composition of claim 18, wherein the pharmaceutically acceptable carrier is an inhibitor of said efflux pump.

* * * * *